United States Patent
Newkirk et al.

(10) Patent No.: US 8,012,512 B2
(45) Date of Patent: Sep. 6, 2011

(54) PURIFICATION OF INOSITOL FROM PLANT MATERIALS

(75) Inventors: Rex W. Newkirk, Winnipeg (CA); David D. Maenz, Saskatoon (CA); Henry L. Classen, Saskatoon (CA)

(73) Assignee: MCN Bioproducts Inc., Saskatoon, Saskatchewan (CA)

( * ) Notice: Subject to any disclaimer, the term of this patent is extended or adjusted under 35 U.S.C. 154(b) by 0 days.

(21) Appl. No.: 10/535,270

(22) PCT Filed: Nov. 28, 2003

(86) PCT No.: PCT/CA03/01849
§ 371 (c)(1),
(2), (4) Date: Feb. 9, 2006

(87) PCT Pub. No.: WO2004/050887
PCT Pub. Date: Jun. 17, 2004

(65) Prior Publication Data
US 2006/0216803 A1    Sep. 28, 2006

(30) Foreign Application Priority Data
Nov. 29, 2002  (CA) ..................................... 2413240

(51) Int. Cl.
*A61K 36/00* (2006.01)
(52) U.S. Cl. ....................................................... 424/725
(58) Field of Classification Search ........................ None
See application file for complete search history.

(56) References Cited

U.S. PATENT DOCUMENTS

| | | | | |
|---|---|---|---|---|
| 4,734,283 A * | 3/1988 | Siren | ............................. | 424/439 |
| 4,777,134 A * | 10/1988 | Siren | ............................. | 435/155 |
| 4,797,390 A * | 1/1989 | Siren | ............................. | 514/103 |
| 5,096,594 A * | 3/1992 | Rabinowitz | .................... | 210/656 |
| 5,554,399 A * | 9/1996 | Vanderbeke et al. | ........... | 426/49 |
| 5,834,286 A * | 11/1998 | Nevalainen et al. | .......... | 435/196 |
| 6,156,563 A | 12/2000 | Kampen | | |
| 2001/0018197 A1 * | 8/2001 | Wong et al. | .................. | 435/68.1 |

FOREIGN PATENT DOCUMENTS

JP  04 365489  12/1992

OTHER PUBLICATIONS

Chen et al, Mechanisms by which wheat bran and oat bran increase stool weight in humans, Am. J. Clin. Nutr 1998; 68: 711-9.*

Nyman et al, Fermentation of dietary fiber in the intestinal tract: comparison between man and rat, British Journal of Nutrition (1986), 55, 487-496.*
Anderson et al, Dietary fiber content of corn bran, Journal of Food Protection, 43 (10): 760-762.*
Theander et al, Studies on dietary fibers. 1. Analysis and chemical characterization of water-soluble and water-insoluble dietary fibers, Swedish Journal of Agricultural Research (1979) 9 (3): 97-106.*
Patent Abstracts of Japan, vol. 0172, No. 36 (C-1057), May 13, 1993.
Kaufman H. W. and Kleinberg I.: "Hydrolysis of Phytate and its Inositol Phosphate Intermediates by an Acid and an Alkaline Phosphatase". Archs Oral Biol., vol. 20, 1975, pp. 157-160, XP000902746, the whole document.
Lim P E et al.: "The Phytases II. Properties of Phytase Reactions F1 and F2 From Wheat Bran and the Myo-Inositol Phosphates Produced by Fraction F2" Biochimica ET Biophysica Acta, Amsterdam, NL, vol. 302, No. 2 E43, 1973, pp. 316-328, XP00972485, ISSN: 0006-3002, the whole document.
Mullaney E J et al: "The term phytase comprises several different classes of enzymes" Biochemnical and Biophysical Research Communications, Academic Press Inc., Orlando, FL, US, vol. 312, No. 1, Dec. 5, 2003, pp. 179-184, XP004473248, ISSN: 0006-291X, the whole document.
Database Chemabs 'Online! Chemical Abstracts Service, Clumbus, Ohio, US; 1998, Pizzoferato, L. et al Pizzoferrato, L. et al: "31P NMR spectra of myo- inositol phosphates in model systems and foods 31P NMR spectra of myo- inositol phosphates in model systems and foods", Database accession No. 1998: 145617, XP000227293, abstract, & Current Status and Future Trends in Analytical Food Chemistry, Proceedings of the European Conference on Food Chemistry, 8th, Vienna, Sep. 18-20, 1995, vol. 3, 644-647. Editor(s): Sontag, Gerhard; Pfannhauser, Werner. Publisher: Austrian Chemica, 1995.
Chen Q-C et al: "Separation of phytic acid and other related inositol phosphates by high-performance ion chromatography and its applications" Journal of Chromatography A, Elsevier Science, NL, vol. 1018, No. 1, Nov. 7, 2003; pp. 41-52, XP004463107, ISSN: 0021-9673, the whole document.
B.Q. Phillippy et al: Preparation of Inositol Phosphates From Soidum Phytate by Enzymatic and Nonenzymatic Hydrolysis, Analytical Biochemistry 162, 115-121 (1987).

* cited by examiner

*Primary Examiner* — Qiuwen Mi
(74) *Attorney, Agent, or Firm* — Daphne L. Maravei; Blake, Cassels & Graydon LLP

(57) ABSTRACT

Phytate and/or phytin and/or phytic acid in an aqueous slurry of plant material is partially hydrolyzed by incubating the slurry with an enzyme product enriched in phytase. The soluble fraction of the slurry is separated into anionic and neutral fractions. The anionic fraction is then hydrolyzed further, and the hydrolyzate is separated into second ionic and neutral fractions. The second neutral fraction thus obtained is rich in inositol, and does not contain significant quantities of other sugars which would be hard to separate from it.

15 Claims, 1 Drawing Sheet

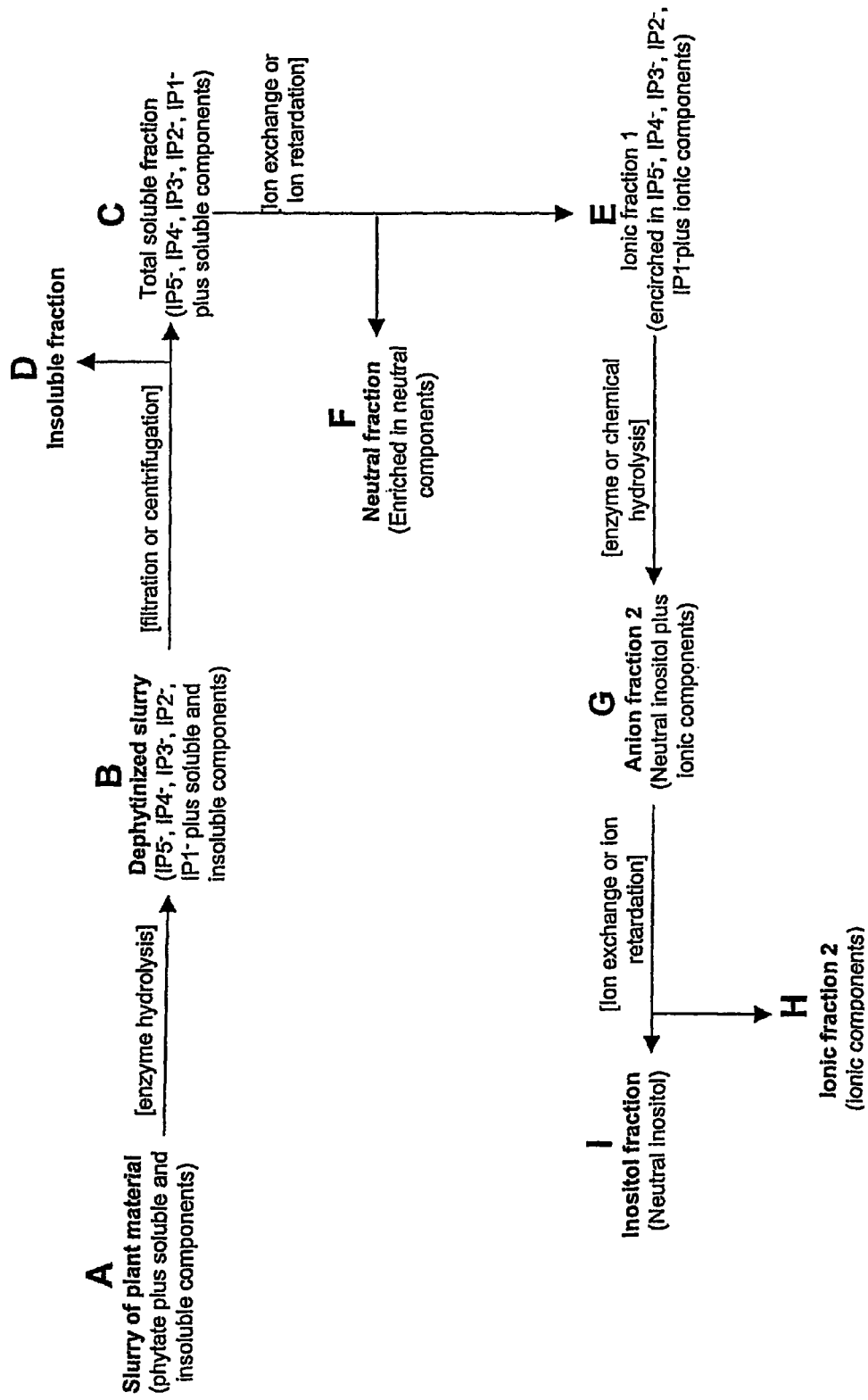
Fig1. Purification of inositol from plant materials

US 8,012,512 B2

PURIFICATION OF INOSITOL FROM PLANT MATERIALS

FIELD OF THE INVENTION

This invention relates to production of inositol from plant materials.

BACKGROUND TO THE INVENTION

Inositol is a highly valued B-vitamin. Plants contain phytic acid {myoinositol 1,2,3,4,5,6-hexakis (dihydrogen phosphoric acid)} as the storage form of phosphorus. Phytic acid is found within plant cell structures as mineral bound complexes termed phytin. Phytin is largely insoluble at neutral pH. Phytic acid can also exist in solution in the salt form termed phytate. The terms "phytin" and phytate are often used interchangeably. In this disclosure, the term "phytate" is intended to refer to phytic acid, phytate and phytin, except where a distinction between these materials is made specifically.

Some of the partial hydrolysis products of phytate are inositol pentaphosphate (IP5), inositol tetraphosphate (IP4), inositol triphosphate (IP3), inositol diphosphate (IP2) and inositol monophosphate (IP1). These partial hydrolysis products of phytate can be hydrolyzed further to yield inositol. The obtaining of inositol from a plant material requires conversion of the phytate to inositol and purification of the inositol from other components in the plant starting material.

Producing inositol from plant material is difficult. One approach is to hydrolyze the phytate in an aqueous slurry, to yield various sugars including inositol. However, inositol is a neutral soluble sugar that is very similar in molecular size and charge characteristics to other sugars such as glucose that are often present in high levels in plant materials. Because of this, it can be difficult to separate the inositol from the other carbohydrates in the slurry.

Another approach to production of inositol from plant materials is to purify the phytate from the starting slurry and to hydrolyze the purified phytate to inositol in a later step in the overall process. However, because phytate in plants usually exists in the form of phytin, direct phytate purification from an aqueous slurry of plant materials requires solubilization of phytin and then separation of the phytate from the remainder of the components of the slurry. Efficient extraction, solubilization of phytin and separation from the remaining components of the slurry is difficult.

DESCRIPTION OF THE INVENTION

This invention describes a useful process for overcoming the inherent difficulties in obtaining inositol from plant materials.

In accordance with the inventive process, phytate in an aqueous slurry of plant material is partially hydrolyzed by incubating the slurry with an enzyme product enriched in phytase. The soluble fraction of the slurry is separated into anionic and neutral fractions. The anionic fraction is then hydrolyzed further, and is in turn separated into ionic and neutral fractions.

The neutral fraction thus obtained is rich in inositol, and does not contain significant quantities of other sugars which would be hard to separate from it.

DESCRIPTION OF THE DRAWINGS

FIG. 1 is a process flow chart depicting processing stages in accordance with the invention.

DETAILED DESCRIPTION OF THE INVENTION

According to the invention, an aqueous slurry of plant material is partially hydrolyzed using phytase enzyme. FIG. 1 shows a process flow chart of the various steps in the process of the invention.

As shown in FIG. 1, an aqueous slurry of plant material A is subjected to partial hydrolysis with phytase. This is preferably done by incubating the aqueous slurry with phytase, at suitable temperature and pH to encourage partial hydrolysis.

The phytase enzyme can hydrolyze phytate to inositol pentaphosphate (IP5), inositol tetraphosphate (IP4), inositol triphosphate (IP3) and inositol diphosphate (IP2). However, the phytase has little activity for hydrolysis of inositol 2-monophosphate inositol (IP1). Acid phosphatase can readily hydrolyze IP1 to free inositol, which is not desired at this point in the inventive process. Thus, the source of phytase used preferably contains little or no acid phosphatase. A source of phytase containing acid phosphatase activity can also be used, if reaction conditions are chosen to favour phytase activity and avoid substantial hydrolysis of IP1 by acid phosphatase. In using a source of phytase containing acid phosphatase the preferred pH of the reaction is greater than 3.0 and less than 7 for optimum phytase activity without substantial hydrolysis of IP1 to inositol.

IP5, IP4, IP3, IP4, IP2 and IP1 are the major products of the reaction. They are highly soluble negatively charged compounds that exist in solution in the partially hydrolyzed slurry (shown as "B" in FIG. 1). The partially hydrolyzed slurry is separated by physical separation means, such as filtration or centrifugation, to generate an inositol phosphate-containing soluble fraction (a "total soluble" fraction called C in FIG. 1) and an insoluble fraction (called "D" in FIG. 1).

Unlike inositol, inositol phosphates have a negative charge. It is therefore possible to separate the total soluble fraction into an anionic fraction and a first neutral fraction, with the inositol phosphates passing into the anionic fraction. Depending on how the separation is carried out, any cationic soluble materials present may remain either with the anionic fraction or the first neutral fraction.

Total soluble fraction C is therefore separated into a first ionic fraction enriched in anionic constituents—called "ionic fraction 1" or "E" in FIG. 1) and a first fraction enriched in neutral constituents (and possibly cationic constituents as well, called "F" in FIG. 1). Ionic fraction 1(E) contains most of the inositol phosphates, and the neutral fraction contains most of the neutral soluble constituents of the total soluble fraction. The separation is done using known techniques for the separation of charged ionic species from soluble neutral compounds in a solution. Such techniques are, for example, ion exchange, ion exclusion, or ion retardation column separations. If it is desired to retain the cationic components in the neutral fraction, a cationic ion exchange resin can be used, which will separate out only the anionic components into the first ionic fraction. If it is desired that the cationic components are separated out as well, then mixed anionic and cationic exchange resins can be used. The important thing at this stage is to end with one fraction which contains the anionic components and a second which contains the neutral components. Cationic components are not of concern in the process of the invention, so they can remain in either fraction.

The next step in the process is to complete the hydrolysis of inositol phosphates in the ionic fraction. This process can be done with enzymes such as phytase or acid phosphatase or without enzyme-based catalysis under controlled conditions of temperature, pressure and pH. Suitable conditions for inositol phosphate hydrolysis are known, and can be chosen according to the particular reaction equipment available. The preferred approach is to use an enzyme source containing acid phosphatase at a pH of less than 4 for optimum activity. Complete hydrolysis of inositol phosphates will generate an anionic fraction (G in FIG. 1) which contains various anionic compounds from fraction E as well as neutral inositol.

Inositol can be separated from the remainder of the soluble compounds in the anionic fraction G using known techniques for separating charged from neutral compounds in solution, such as, for example, an ion exchange, ion exclusion or ion retardation column. This process generates a second ionic fraction (—called herein ionic fraction 2, and indicated in FIG. 1 as "H"). and a second neutral I fraction ("I" in FIG. 1) rich in inositol. The inositol in the second neutral fraction can then be concentrated, crystallized and dried to form a final dry purified inositol product.

The invention has been described by reference to preferred embodiments, but it will be understood that other embodiments will be evident to a person skilled in the art. It is therefore desired that the invention shall not be limited by the particular embodiments shown, but shall include such other embodiments as would occur to a skilled person.

What is claimed is:

1. A process for producing inositol from plant materials comprising the steps of:
   a) providing a plant material comprising a neutral soluble sugar and at least one of a phytate or a phytin;
   b) providing an aqueous slurry of said plant material from step a),
   wherein said aqueous slurry of said plant material comprises said neutral soluble sugar of said plant material and said at least one of a phytate or a phytin of said plant material;
   c) conducting a partial hydrolysis by treating said aqueous slurry of said plant material resulting from step b) with an enzyme product enriched in phytase enzyme to partially hydrolyze said at least one of a phytate or a phytin to produce a partially hydrolyzed slurry comprising a mixture of inositol phosphates which are negatively charged, and wherein said plant material is a main source of the phytate or phytin which is partially hydrolyzed during said step of a partial hydrolysis;
   d) separating said partially hydrolyzed slurry of said plant material resulting from step c) to produce a water soluble fraction and a water-insoluble fraction, wherein said water soluble fraction comprises inositol phosphates which are negatively charged, as well as said neutral soluble sugar of said plant material;
   e) separating said water soluble fraction resulting from step d) into a first ionic fraction comprising inositol phosphates which are negatively charged and a first neutral fraction comprising said neutral soluble sugar of said plant material;
   f) conducting a hydrolysis of said inositol phosphates of said first ionic fraction resulting from step e) to produce inositol and an anionic fraction; and
   g) separating said inositol from said anionic fraction resulting from step f.

2. The process of claim 1, wherein said enzyme product in step c) does not include an acid phosphatase.

3. The process of claim 1 wherein said step of treating the aqueous slurry in step c) is carried out at a pH between about 3.0 and about 7.0.

4. The process of claim 3, wherein said enzyme product in step c) comprises an acid phosphatase.

5. The process of claim 1, wherein said step of separating the partially hydrolyzed slurry into a water-soluble fraction and a water-insoluble fraction in step d) is carried out by centrifugation.

6. The process of claim 1, wherein said step of separating the partially hydrolyzed slurry into a water-soluble fraction and a water-insoluble fraction in step d) is carried out by filtration.

7. The process of claim 1, in which the step of conducting a hydrolysis of said inositol phosphates of said first ionic fraction in step f) comprises treating said first ionic fraction with a phytase.

8. The process of claim 1, in which the step of conducting a hydrolysis of said inositol phosphates of said first ionic fraction in step f) comprises treating said first ionic fraction with an acid phosphatase.

9. The process of claim 8, wherein said step of conducting a hydrolysis in step f) is carried out at a pH of less than 4.

10. The process of claim 3, in which the step of conducting a hydrolysis of said inositol phosphates in said first ionic fraction in step f) comprises treating said first ionic fraction with a phytase.

11. The process of claim 3, in which the step of conducting a hydrolysis of said inositol phosphates in said first ionic fraction in step f) comprises treating said first ionic fraction with acid phosphatase.

12. The process of claim 11, wherein said step of conducting a hydrolysis in step f) is carried out at a pH of less than 4.

13. The process of claim 4, in which the step of conducting a hydrolysis of said inositol phosphates in said first ionic fraction in step f) comprises treating said first ionic fraction with acid phosphatase, and wherein said hydrolysis is carried out at a pH of less than 4.

14. The process of claim 1, wherein the step of conducting a hydrolysis of inositol phosphates of said first ionic fraction in step f) is achieved free of enzyme based catalysis.

15. The process of claim 1, further comprising the step of producing a product comprising said inositol resulting from step g).

* * * * *